US010822625B2

(12) United States Patent
Tong et al.

(10) Patent No.: US 10,822,625 B2
(45) Date of Patent: Nov. 3, 2020

(54) METHOD FOR DOMESTICATING *SACCHAROMYCES CEREVISIAE*

(71) Applicants: COFCO (Jilin) Bio-Chemical Technology Co., Ltd., Jilin (CN); COFCO Bio-Energy (Zhaodong) Co., Ltd., Zhaodong, Heilongjiang (CN); Nutrition & Health Research Institute, COFCO Corporation, Beijing (CN)

(72) Inventors: Yi Tong, Beijing (CN); Yi Li, Beijing (CN); Junqi Zhang, Zhaodong (CN); Taibo He, Beijing (CN); Zexing Wang, Zhaodong (CN); Bo Hou, Zhaodong (CN); Hui Liu, Zhaodong (CN); Fan Li, Beijing (CN); Lida Wu, Jilin (CN)

(73) Assignees: COFCO (JILIN) BIO-CHEMICAL TECHNOLOGY CO., LTD., Jilin (CN); COFCO BIO-ENERGY (ZHAODONG) CO., LTD., Zhaodong (CN); NUTRITION & HEALTH RESEARCH INSTITUTE, COFCO CORPORATION, Beijing (CN)

( * ) Notice: Subject to any disclaimer, the term of this patent is extended or adjusted under 35 U.S.C. 154(b) by 0 days.

(21) Appl. No.: 16/700,404

(22) Filed: Dec. 2, 2019

(65) Prior Publication Data
US 2020/0172938 A1 Jun. 4, 2020

(30) Foreign Application Priority Data

Nov. 30, 2018 (CN) .......................... 2018 1 1453266

(51) Int. Cl.
*C12P 7/14* (2006.01)
*C12R 1/865* (2006.01)
(52) U.S. Cl.
CPC ................ *C12P 7/14* (2013.01); *C12R 1/865* (2013.01)

(58) Field of Classification Search
None
See application file for complete search history.

(56) References Cited

U.S. PATENT DOCUMENTS

2015/0307872 A1* 10/2015 Sato ..................... C07K 14/395
435/165

FOREIGN PATENT DOCUMENTS

| CN | 103205368 A | | 7/2013 | |
|---|---|---|---|---|
| CN | 104450598 A | * | 3/2015 | ............... C12N 1/36 |

* cited by examiner

*Primary Examiner* — Nghi V Nguyen
(74) *Attorney, Agent, or Firm* — Duane Morris LLP

(57) ABSTRACT

The present disclosure provides a method for domesticating *Saccharomyces cerevisiae* which is resistant to fermentation inhibitors, high temperature and high concentration of ethanol. The method comprises a primary domestication and a secondary domestication of the *S. cerevisiae*, wherein the primary domestication comprises the steps of replacing the fermented mash with fresh liquefied mash and continuing fermentation when the ethanol content in the fermented mash reaches a higher concentration (>12% (v/v)), the replacement is performed for at least 20 times, and the time interval of replacements is 20-30 hours; the secondary domestication comprises the steps of performing high-temperature domestication on the primary domesticated strain by a temperature gradient and replacing the fermented mash for multiple times, wherein the temperature is raised by 0.5° C.-2° C. every 18-24 times of replacement. The domesticated *S. cerevisiae* in the present disclosure not only adapts to the fermentation conditions of factories, resists the fermentation substrate-inhibitors, but also maintains high production capacity of ethanol, and is still efficiently propagated and metabolized in a higher temperature environment, such that the ethanol fermentation level of enterprises can be improved without modifying process routes and conditions.

15 Claims, 1 Drawing Sheet

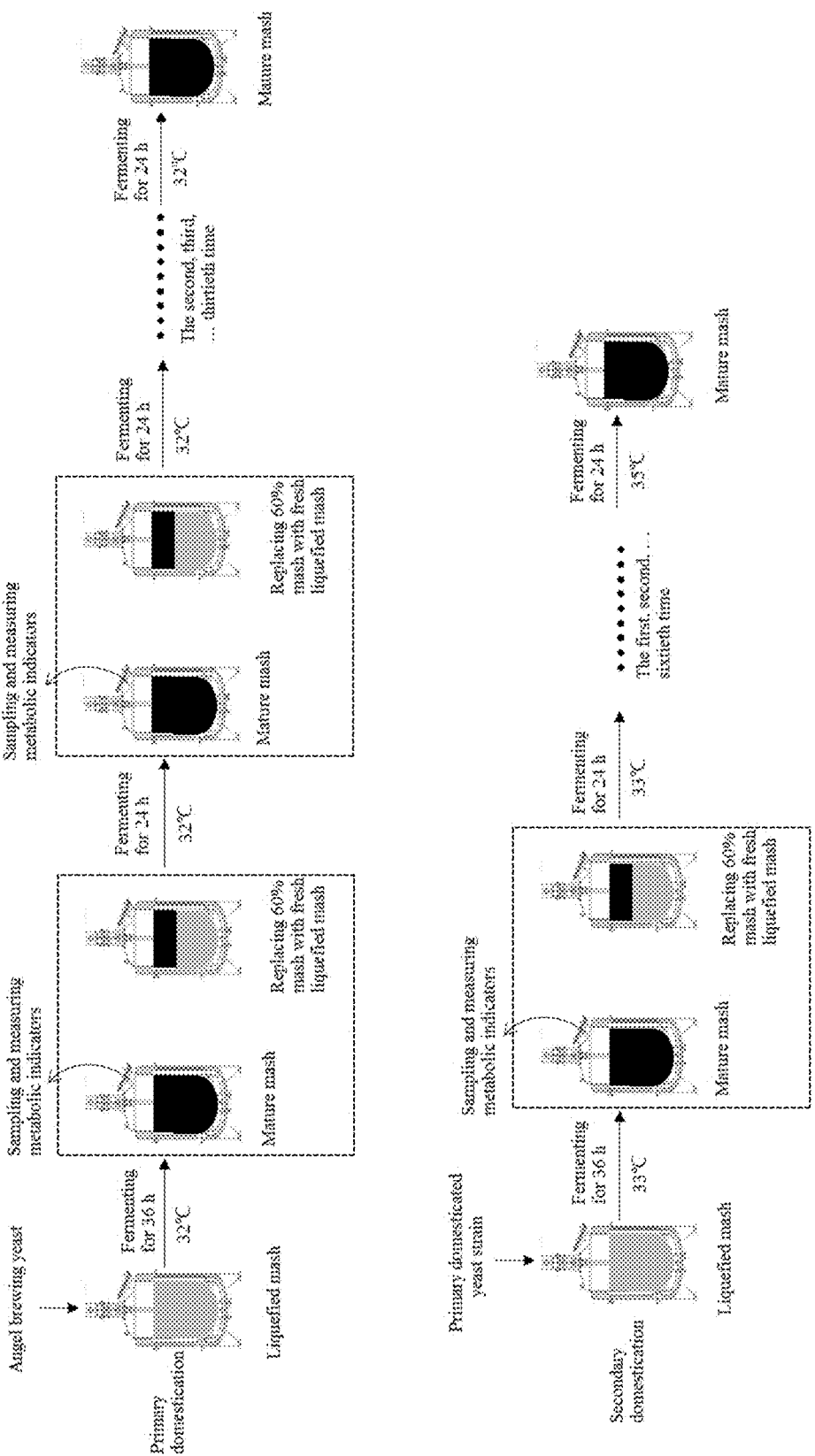

METHOD FOR DOMESTICATING *SACCHAROMYCES CEREVISIAE*

PRIORITY CLAIM & CROSS REFERENCE

The application claims priority to Chinese Application No. 201811453266.6, filed on Nov. 30, 2018, entitled "Domesticating method for industrial *Saccharomyces cerevisiae*", which is herein specifically and entirely incorporated by reference.

FIELD

The present disclosure belongs to the technical field of bioengineering and microorganism, and particularly relates to a method for domesticating *S. cerevisiae* which is resistant to inhibitors in an industrial fermentation process for ethanol, resistant to high concentration of ethanol and resistant to high temperature.

BACKGROUND

Ethanol is an important raw material in food and chemical industries and also an oxygen-containing additive of the automotive gasoline. In China, starchy crops such as corn, cassava, wheat and rice are mainly taken as raw materials, and yeast are used for fermentation strain so as to produce ethanol during the ethanol fermentation production. The ethanol fermentation process is a process in which the yeast utilizes fermentable sugars in a culture medium to produce ethanol and release carbon dioxide under a proper temperature and anaerobic condition. The entire ethanol fermentation production process may be divided into the working procedures including crushing raw material, blending material, liquefaction, saccharification, fermentation, distillation and the like. In the last two decades, the domestic ethanol fermentation production process has been upgraded from stepwise saccharification and fermentation in the past to simultaneous saccharification and fermentation due to the continuous improvement of production and performance of the saccharifying enzyme. At present, the domestic simultaneous saccharification and fermentation processes mainly include two types of fermentation, namely batch fermentation and continuous fermentation. On the other hand, the industrial *S. cerevisiae* in the form of active dry yeast powder are widely applied in the ethanol fermentation and production, so that the tedious steps of stepwise amplifying and culturing the yeast are eliminated. The active dry yeast powder can be directly added into a fermentation tank for fermentation, or being inoculated into the fermentation tank for fermentation after enlarging culture in an activation tank and a seeding yeast tank. After the ethanol fermentation is completed, the fermented mash is generally distilled to purify the product ethanol, a part of clear liquid obtained by separating the obtained waste lees is used for recycling and blending with the materials, and the remaining clear liquid and the wet lees are used for producing stillage feedstuff DDGS (distillers dried grains with soluble).

The industrial *S. cerevisiae* is a yeast variety obtained through long-time breeding, and has the advantages of quick propagation, high ethanol yield and strong resistance in severe environment. The fermentation production factories of the ethanol have more or less differences in the aspects of used raw materials, mixing concentration, fermentation mode and fermentation conditions, recycling and blending proportion of clear liquid of fermented waste lees, and the specific fermentation environments are also significantly different. As for ethanol fermentation manufacturers, the active dry yeast powder is only applied as a production auxiliary material for being put into use at one time. Thus, there are circumstances where the yeast strains have differences in their adaptability to the unique fermentation environment of each manufacturer, in particular, the yeast strains have limited tolerance to inhibitors from the raw material and the recycling and blending clear liquid in the fermented mash, thereby affecting activity of the yeast strain and then influence its ethanol tolerance and ethanol production efficiency. In the high-temperature period in summer, because the yeast strains have insufficient temperature tolerance, the hidden danger that the thalli die too fast and are not completely fermented easily occurs, and a large amount of cooling water is needed for lowering temperature. For example, when the commercial yeast strain-Angel super brewing-high activity-dry yeast with desirable performance in China is fermented at a temperature of 31-33° C. by different domestic manufacturers (the fermentation time is between 60-80 hours), the volume percentage of ethanol at the end of fermentation is within a range of 11-15% (v/v). As can be seen, the same yeast strains exhibit a large difference in fermentation performance when they are used by different manufacturers.

The above differences are mainly resulting from that the ethanol fermentation manufacturers do not refer to the unique fermentation environments (e.g., materials and fermentation conditions) to perform targeted domestication and screening of commercialized yeasts before the fermentation production, that is, the fermentation potential of yeast has not been discovered and utilized. By virtue of the characteristics of rapid propagation and mutation evolution under certain pressure of microorganisms, the commercial yeast strains can be domesticated and screened by using industrial fermentation raw materials under the condition of simulating actual fermentation conditions, thereby obtaining the yeast strains with environmental adaptability, tolerance and excellent fermentation performance in regard to the unique production environment of individual ethanol fermentation manufacturer. The method improves the ethanol fermentation level of enterprises based on the premise of not changing the ethanol fermentation process, route and conditions.

Regarding the domestication method of yeast, CN103205368A discloses a domestication method for high temperature resistant, ethanol-tolerant, aroma-producing yeast. The method comprises the following steps: screening a yeast strain with an excellent aroma-producing property from commercially available aroma-producing yeasts; uniformly mixing an aroma-producing yeast liquid in a logarithmic phase with an aqueous solution of sodium alginate at a room temperature under a germ-free condition, adding a mixed liquor into an aqueous solution of calcium chloride to prepare a gel ball particle and immobilizing the gel ball particle at a temperature of 2-4° C. for 4-5 hours so as to obtain an immobilized gel particle; subjecting an obtained immobilized aroma-producing yeast to high temperature-resistant and ethanol-tolerant cyclic gradient domestication in an ethanol domestication medium and carrying out cyclic domestication for a plurality of times so as to obtain the high temperature-resistant and ethanol-tolerant aroma-producing yeast. Although the method adopts a circulating gradient domestication method, the used ethanol domestication culture medium is formed by mixing ethanol and a YEPD liquid culture medium with rich nutrition, and the ethanol domestication culture medium contains less sugar and is significantly different from the environment in industrial ethanol fermentation. Thus, the static tolerance to temperature and ethanol of the yeast obtained by this method may be improved, but the dynamic fermentation performance such as fermentation rate and ethanol yield is not yet known. In addition, the present disclosure does not provide a method for improving the tolerance of yeast to fermentation inhibitors encountered in industrial production processes. As a result, the tolerance of the yeasts obtained by this process in regard to the temperatures and ethanol concentrations in practical industrial ethanol fermentations is necessarily greatly compromised.

In addition, CN104450598A discloses a method for domesticating S. cerevisiae, specifically, the method comprises: cultivating the S. cerevisiae in a mixture of sweet mash of corn and enzymolysis liquid to obtain small seeding yeast, wherein a mass ratio of the sweet mash of corn to the enzymolysis liquid is (80-90): (10-20); performing multi-generation enlarge culture on the small seeding yeast in the mixture of sweet mash of corn and enzymolysis liquid to obtain large seeding yeast, in the enlarge culture for each generation of the large seeding yeast, the proportion of enzymolysis liquid is gradually increased until the mass ratio of the enzymolysis liquid in the mixture reaches 85-95%, and the tolerance to the enzymolysis liquid, five-carbon sugar metabolic capability and the ethanol yield of the domesticated yeast strains are improved. The method for gradually increasing the concentration of the target fermentation substrate by repeating the culture operation improves the tolerance degree of the yeast to the inhibitor in the target fermentation substrate, however, the domestication time of the yeast in the mixture is limited (only 8-12 hours), and the concentration of ethanol generated in the domestication process is far lower than that of industrial ethanol production, thus the method cannot improve the tolerance of the yeast strain to high-concentration of ethanol generated in industrial fermentation. In addition, the development of the corn-ethanol production technology in China is in a standstill, an improvement on this technology is urgently needed to enhance the efficiency of ethanol production.

Therefore, there is an urgent need in the ethanol fermentation industry to develop a method for domesticating the S. cerevisiae which is fermentation substrate-inhibitor-tolerant, high temperature-resistant and ethanol-tolerant, so that a yeast strain for ethanol fermentation industry can be obtained, which meets the requirements of industrial application, is specifically adapted to the fermentation environment (e.g., materials and fermentation conditions) of each ethanol production enterprise, and has excellent inhibitor tolerance, high-concentration ethanol tolerance, high-temperature tolerance and fermentation performance.

SUMMARY

The present disclosure aims to provide a method for domesticating S. cerevisiae which is resistant to fermentation inhibitors, high temperature and high-concentration of ethanol, so as to obtain a S. cerevisiae strain which is resistant to fermentation substrate-inhibitors, high temperature and high-concentration of ethanol.

Therefore, the present disclosure provides a method for domesticating (or acclimating, or habituating, or taming) S. cerevisiae, comprising:

1) activating the starting S. cerevisiae;
2) preparing a mature mash of seeding yeast of the starting S. cerevisiae using a liquefied mash;
3) performing a primary domestication on the S. cerevisiae: mixing the mature mash of seeding yeast in step 2) with a liquefied mash and fermenting the mixture until the ethanol concentration in the fermented mash reaches 12% (v/v) or more, preferably 13% (v/v) or more, replacing the fermented mash with fresh liquefied mash and continuing fermentation to obtain a primary domesticated mash, wherein the replacement is performed for at least 20 times, preferably at least 30 times, the replacement proportion is 55 vol %-80 vol %, preferably 60 vol %-70 vol % of the fermented mash, and the time interval of replacements is 20-30 hours; and separating and purifying the S. cerevisiae in the primary domesticated mash, and screening a S. cerevisiae strain with improved fermentation performance compared with a reference level as a primary domesticated yeast strain;

4) preparing a mature mash of seeding yeast of the primary domesticated yeast strain using a liquefied mash;

5) performing secondary domestication on the S. cerevisiae: mixing the mature mash of seeding yeast of the primary domesticated yeast strain obtained in step 4) with a liquefied mash, and fermenting the mixture until the ethanol concentration in the fermented mash reaches 12% (v/v) or more, preferably 13% (v/v) or more, replacing the fermented mash with fresh liquefied mash under a temperature gradient, and continuing fermentation, wherein the replacement proportion is 55 vol %-80 vol %, preferably 60 vol %-70 vol % of the fermented mash, the time interval of replacements is 20-30 hours, the lowest temperature of the temperature gradient is 28° C.-33° C., the highest temperature of the temperature gradient is 34° C.-38° C., the amplification of the temperature gradient is 0.5° C.-2° C. for every 18-24 times of replacement, thereby obtaining a S. cerevisiae strain which is resistant to high temperature, ethanol and fermentation substrate-inhibitors, wherein the liquefied mash is derived from starchy biomass, and wherein the liquefied mash is added with the saccharifying enzymes.

In the present disclosure, the starting S. cerevisiae is Angel brewing-dry yeast, preferably Angel super brewing-high activity-dry yeast.

Favorable Effects

The domestication method of the present disclosure is simple and convenient to operate, has excellent reproducibility, and be capable of screening the S. cerevisiae which is resistant to the fermentation substrate-inhibitor, high-temperature and high concentration of ethanol. The obtained strain has the advantages of rapid growth and reproduction, strong production capacity of ethanol and suitability for industrial fermentation production of ethanol.

BRIEF DESCRIPTION OF THE DRAWINGS

FIG. 1 is a schematic flow chart of primary domestication and secondary domestication of an embodiment of the present disclosure.

DETAILED DESCRIPTION

The embodiments of the present disclosure will be described below in detail with reference to the accompanying drawings, but the protection scope of the present disclosure is not limited thereto.

In addition to the ethanol and $CO_2$ produced during the ethanol fermentation of starchy raw material, the byproducts such as acetaldehyde, formic acid, acetic acid, lactic acid, glycerol, fusel oil are also generated. Moreover, the furfural, hydroxymethyl furfural, amino sugar and the like are also generated by the decomposition reaction and the Maillard reaction in the process of boiling and gelatinizing the raw materials. These byproducts have certain inhibiting effect on the growth and reproduction of the yeast. The improved resistance of the strain in regard to the fermentation substrate-inhibitor may be mainly reflected by the number of living cells and the death rate in the fermented mash. With respect to strain domestication, if the domesticated strain is not improved in the tolerance to fermentation inhibitors, its cell number and cell death rate at the end of fermentation are essentially the same as those prior to the domestication, thus it will not cause an increased ethanol concentration in the mature mash. If the strain is not resistant to high temperature, the mortality of the strain increases, so that the fermentation is difficult to be sufficiently performed, thus the result indicates that the final ethanol concentration may not be increased or even reduced. In the present disclosure, the mature mash means a fermented mash obtained at the end of the ethanol fermentation. In the present disclosure, the terms mature mash and fermented mash may be used interchangeably. Therefore, the ethanol concentration in the mature mash is mainly used as an indicator in the domestication process of the present disclosure.

In this context, the term "mature mash of seeding yeast" refers to a culture solution of *S. cerevisiae* obtained by the enlarge culture of *S. cerevisiae* in an ethanolic fermentation process, which is capable of being fermented in a fermentation tank. Typically, the number of *S. cerevisiae* in a mature mash of seeding yeast is $1.2 \times 10^8$-$1.5 \times 10^8$ CFU/mL.

The term "high concentration of ethanol" herein in the industrial production of ethanol means that the ethanol concentration in the fermented mash reaches 14% (v/v) or more.

In the present disclosure, the starchy biomass is selected from the group consisting of corn, tapioca, wheat or rice, sugarcane, sweet sorghum and the like.

High temperature resistance herein means that the *S. cerevisiae* is resistant to culture temperatures of 33° C.-38° C.

In the present disclosure, the starting *S. cerevisiae* may be any strain of *S. cerevisiae*. For example, the starting *S. cerevisiae* strain may be a commercially available strain, such as Angel *S. cerevisiae* dry yeast. In an embodiment of the present disclosure, the starting *S. cerevisiae* is preferably Angel super brewing-high activity-dry yeast. In addition, the starting *S. cerevisiae* may be a mutagenized or genetically engineered *S. cerevisiae*.

In step 1), the *S. cerevisiae* strain may be activated by using a known method in the art. For example, in regard to the *S. cerevisiae* in the form of dry yeast powder, it may be activated with sterile water. The *S. cerevisiae* frozen with glycerol may be activated by subjecting the strain liquid to streak inoculation on a culture medium plate and culturing, wherein the culture temperature is within a range of 30-32° C. and the culture time is 12-36 hours. For example, the culture temperature for activation may be 28° C., 29° C., 30° C., 31° C. or 32° C. For instance, the culture time for activation may be 12 hours, 14 hours, 16 hours, 18 hours, 20 hours, 22 hours, 24 hours, 26 hours, 28 hours, 30 hours, 32 hours, 34 hours, or 36 hours. The culture medium plate may be a culture plate for *S. cerevisiae* (e.g., YEPD plate, YPD plate) commonly used in the art. In addition, with respect to the genetically engineered *S. cerevisiae*, the culture medium plate may also be selected by using plate containing antibiotics and/or plate of yeast auxotroph depending on the genotype thereof.

In a preferred embodiment of the present disclosure, 10 g of dry powder of *S. cerevisiae* is activated in 200 mL of sterile water, the activation temperature is 30-33° C., and the activation time is 20-30 min.

In step 2), the liquefied mash derived from starchy biomass may be a liquefied mash used in the art for industrial ethanol fermentation. The starchy biomass may be selected from a group consisting of corn, tapioca, wheat, rice, sugar cane, sweet sorghum and the like. In the present disclosure, the starchy biomass is preferably corn.

Accordingly, a starchy biomass-derived liquefied mash can also be prepared with the methods disclosed in the art. Wherein, taking corn as an example, the liquefied mash of corn can be prepared with the following method: mixing corn powder and water (the mass ratio of the material to the water is 1:1.7-1:2.1) to prepare uniform powder slurry, heating for precooking (precooking for 10 minutes at a temperature of 80° C.) to ensure that the starch absorbs water and swells, heating the slurry to a temperature of 85±1° C. and holding for 20-30 minutes, then adding amylase to liquefy at the temperature of 80-85° C. for 3-4 hours, thereby obtaining the liquefied mash of corn. In a preferred embodiment of the present disclosure, the liquefied mash of corn has a dry solid content of 30 wt %. The liquefied mash typically further contains oligosaccharides (oligosaccharides, such as maltose, maltotriose and the like).

In the present disclosure, the dry solid (also referred to as dry matter) content means that the dried mass accounts for a percentage of the mass of the sample before drying, wherein the test sample is dried at a given temperature and time until the test sample is dried to a constant weight. In the present disclosure, the temperature used in measuring dry solid may be about 130° C. and the drying time may be 40 min or more.

In the present disclosure, the liquefied mash derived from the starchy biomass may be liquefied mash which is directly used in industrial fermentation of ethanol. The domestication is implemented by means of the liquefied mash directly used in the industrial ethanol fermentation, and the obtained strain has certain tolerance to fermentation substrate-inhibitors in the industrial ethanol fermentation using the liquefied mash.

In the present disclosure, the liquefied mash contains saccharifying enzymes. For example, in regard to a liquefied mash of corn, it may contain 122,000-126,000 U/kg (liquefied mash), preferably 125,000 U/kg (liquefied mash) of saccharifying enzymes. In some embodiments, the liquefied mash of corn further comprises a protease. For example, the liquefied mash of corn comprises 3,000-4,000 U/kg (liquefied mash), preferably 3,500 U/kg (liquefied mash) of protease. In a further embodiment, the liquefied mash of corn also contains 3 ppm of penicillin.

The saccharifying enzyme is an exoamylase, which hydrolyzes alpha-1,4-glucosidic bonds of the starch one by one from non-reducing end to generate glucose, and can also slowly hydrolyze alpha-1,6-glucosidic bonds to convert into glucose. In a preferred embodiment, the saccharifying enzyme may be saccharifying enzyme commercially available from the Novozymes (China) Biotechnology co., Ltd. in an added amount of 122,000-126,000 U/kg (liquefied mash), preferably 125,000 U/kg (liquefied mash). The protease can hydrolyze protein contained in the corn, increase content of the alpha-amino acid in liquefied mash, and provide rich nitrogen source for growth and propagation of yeast cells. In a preferred embodiment, the protease is a protease from the Shandong Longda Bio-products Co., Ltd. in an added amount of 3,000-4,000 U/kg (liquefied mash), preferably 3,500 U/kg (liquefied mash). Penicillin is a kind of antibiotic, can destroy the cell wall of bacteria and kill the bacteria in the propagation period of the bacteria cells, and plays a role of inhibiting the growth of miscellaneous bacteria in the industrial production of ethanol. In a preferred embodiment, penicillin is commercially available from the North China pharmaceutical Co., Ltd. with an added amount of 3 ppm.

The saccharifying enzymes, proteases, and penicillins may be added into the liquefied mash and mixed together before use, the liquefied mash is then added to a yeast tank and/or domestication fermentation tank. Alternatively, the saccharifying enzyme, protease, penicillin and the liquefied mash may be added into the yeast tank and/or domestication fermentation tank separately.

The mature mash of seeding yeast in step 2) may be prepared with the methods well-known in the art. As an example, the culture conditions for mature mash of seeding yeast are as folllows: inoculating the activated $S.$ cerevisiae into the liquefied mash in a cell number of $1.3 \times 10^8$-$1.5 \times 10^8$ CFU/mL, culturing at a temperature of 28-30° C., a pH of 4.0-5.0, a stirring rate of 100-200 rpm, and introducing sterile air at a rate of 400-550 m$^3$/h for 8-12 hours. In a preferred embodiment, the preparation of the mature mash of seeding yeast is performed in a seeding yeast tank. In one embodiment, the culture conditions in the seeding yeast tank are as follows: the temperature is 29±1° C., the pH is within a range of 4.0-5.0, the stirring rate is 200 rpm, the sterile air is introduced at a rate of 480 m$^3$/h, and the culture time is 10 hours.

The dry yeast powder can be inoculated directly into the liquefied mash after activation.

The domestication method of the present disclosure may further comprise a step of enlarge culture of the activated $S.$ cerevisiae prior to the preparation of $S.$ cerevisiae. The enlarge culture is typically performed in a liquid culture medium and/or a liquefied mash, for example, a YEPD liquid culture medium, a YPD liquid culture medium, or a starchy biomass-derived liquefied mash.

In a preferred embodiment, the enlarge culture is a two-stage enlarge culture. For example, the primary enlarge culture is carried out in a YEPD liquid culture medium or a YPD liquid culture medium under the following culture conditions: the stirring speed is 80 rpm, the temperature is 32° C., and the time is 8 hours; the secondary enlarge culture is performed in a YEPD liquid culture medium, or a YPD liquid culture medium, or a liquefied mash of corn, and the culture conditions are as follows: the rotation speed is 80 rpm, the temperature is 32° C., and the culture is carried out for 12 hours. Wherein, after two-stage enlarge culture, the cell number of the $S.$ cerevisiae may reach $2 \times 10^8$/mL or more.

In a specific embodiment, the colonies with larger diameter and plump shape are picked from a YEPD solid culture medium or a YPD solid culture medium and inoculated into a YEPD liquid culture medium or a YPD liquid culture medium for performing a primary enlarge culture (the stirring speed is 80 rpm, the temperature is 32° C. and the time is 8 hours); then the fermentation liquid obtained by the primary enlarge culture is inoculated to the liquefied mash of corn in a volume ratio of 1:3 for performing a secondary enlarge culture in a 1 L shake flask (conditions of the enlarge culture: the rotation speed is 80 rpm, the temperature is 32° C., the culture time is 12 hours).

In step 3), performing a primary domestication on the $S.$ cerevisiae: mixing the mature mash of seeding yeast in step 2) with the liquefied mash and fermenting the mixture until the ethanol concentration in the fermented mash reaches 12% (v/v) or more, preferably 13% (v/v) or more, replacing the fermented mash with fresh liquefied mash and continuing fermentation to obtain primary domesticated mash, wherein the replacement is performed for at least 20 times, preferably at least 30 times, the replacement proportion is 55 vol %-80 vol %, preferably 60 vol %-70 vol % of the fermented mash, and the time interval of the replacements is 20-30 hours; and separating and purifying the $S.$ cerevisiae in the primary domesticated mash, and screening a $S.$ cerevisiae strain with improved fermentation performance compared with a reference level as a primary domesticated yeast strain;

The mature mash of seeding yeast may be mixed with the fresh liquefied mash at a volume ratio of (20-40):(80-60) in step 2). The mixing ratio is not particularly limited in the present disclosure as long as the ethanol concentration in the fermented mash can reach 12% (v/v) or more, preferably 13% (v/v) or more. For example, in the primary domestication, the mixing ratio of mature mash of seeding yeast of the initial $S.$ cerevisiae and the fresh liquefied mash may be (20-40):(80-60), preferably (25-35):(65-75), more preferably (25-30):(70-75). For example, in the primary domestication, the mature mash of seeding yeast of the initial $S.$ cerevisiae may be mixed with the fresh liquefied mash in a ratio of 20:80, 23:77, 25:75, 30:70, 32:68, 35:65, 37:63, 40:60.

During the domestication process, the fermentation time for the ethanol concentration in the mash to reach 12% (v/v), preferably 13% (v/v) or more for the first time is usually 30-40 hours, for example, 36 hours. In this case, the amount of the thalli can reach $1.2 \times 10^8$-$1.5 \times 10^8$/mL.

In the present disclosure, the replacement of the liquefied mash is carried out after the ethanol concentration in the mash to be fermented reaches a certain value (for example, 12% (v/v), preferably 13% (v/v) or more), such that the yeast is forced to be in a state of subjecting to persecution of high-concentration of ethanol, the yeast which is not tolerant to persecution of ethanol dies, and the yeast which is tolerant to ethanol survives and propagates the next generation. After multiple cycles, the surviving yeast after the screening process may tolerate high-concentration of ethanol; because the yeast is in a high-sugar environment for a long time, the growth and reproduction of the domesticated yeast are expedited.

In the later stage of fermentation, the concentration of ethanol in the fermented mash reaches 12% or more, the reducing sugar available for yeast is little, and the inhibitor generated by fermentation is increased, so that the yeast cells exhibits the reduced activity and begin to die. Therefore, the replacement process is started after the ethanol concentration in the fermented mash reaches 12% or more. In the primary domestication, the replacement proportion is 55 vol %-80 vol % of the fermented mash, i.e., 55 vol %-80 vol % of the fermented mash is replaced with fresh liquefied mash. In an embodiment of the present disclosure, the replacement proportion may be 55 vol %-80 vol %, preferably 60 vol %-70 vol %, e.g. 55 vol %, 56 vol %, 57 vol %, 58 vol %, 59 vol %, 60 vol %, 61 vol %, 62 vol %, 63 vol %, 64 vol %, 65 vol %, 67 vol %, 68 vol %, 69 vol %, 70 vol %, 71 vol %, 72 vol %, 73 vol %, 74 vol %, 75 vol %, 77 vol %, 78 vol %, 79 vol % or 80 vol % of the fermented mash.

In the primary domestication, the time interval of replacing liquefied mash is 20-30 hours. The time interval is primarily dependent on the time when the ethanol concentration in the fermented mash again reaches 12% (v/v) or more, preferably 13% (v/v) after replacing liquefied mash is performed, so as to place the *S. cerevisiae* in an environment of subjecting to persecution of ethanol. Typically, the ethanol concentration in the fermented mash will again reach 12% (v/v) or more, preferably 13% (v/v), within 20 hours after replacing the fermented mash in a ratio of 55 vol %-80 vol %. For example, the time interval of replacement may be 20 hours, 20.5 hours, 21 hours, 21.5 hours, 22 hours, 22.5 hours, 23 hours, 23.5 hours, 24 hours, 24.5 hours, 25 hours, 25.5 hours, 26 hours, 26.5 hours, 27 hours, 27.5 hours, 28 hours, 28.5 hours, 29 hours, 29.5 hours, or 30 hours.

The selective evolution of yeast cells is a slow process, the domestication fail to play a role of stress screening if the domestication time period is short under the same conditions, thus the domestication time period is selected to be at least 3 weeks, preferably 1 month or more or even longer.

In the present disclosure, the number of times for replacement may be at least 20, preferably at least 30. In some embodiments, the number of times for replacement may be at least 20, preferably at least 30, for example, 20, 21, 22, 23, 24, 25, 26, 27, 28, 29 or 30. In some embodiments, the number of times for replacement may be 30 or more, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64 or 65.

In the present disclosure, the ratio of each replacement may be identical or different. In order to enable the yeast cells to adapt to a new environment as soon as possible after the mash is replaced and reduce the persecution of inhibitors to the yeast, the replacement proportion of mash at the early stage may be relatively large; after the domestication for a period of time, the yeast slowly adapts to the persecution environment, the replacement proportion is reduced at the moment, the concentration of the residual inhibitor in the mash is relatively increased, and the nutrient content is reduced, so that the yeast cells are forced to be hungry and subject to the persecution of inhibitors whose content is gradually increased, thereby playing a role of domestication. Therefore, in an embodiment of the present disclosure, the replacement of the fermented mash with fresh liquefied mash is performed by using a larger replacement ratio (e.g., 60 vol %-80 vol %) in the early stage of the primary domestication (e.g., 15-30 times) and a smaller replacement ratio (e.g., 50 vol %-65 vol %) in the later stage of the primary domestication (e.g., 20-65 times).

The isolation and purification of *S. cerevisiae* of the mash following the primary domestication may be performed by using a well-known methods in the art. For example, a fermented mash containing thalli is spread on a solid culture medium plate and culturing, and then a single colony is obtained. In the embodiments of the present disclosure, the plate cultures may be performed for many times in order to obtain a single colony. The fermented mash may be diluted and/or filtered prior to spreading on the plate.

In the present disclosure, the ethanol yield refers to the ethanol concentration (vol) in the fermented mash at the end of the ethanol fermentation process. In an embodiment, an appropriate amount of 65% sulfuric acid is added to the fermented mash sample to inactivate the enzyme and adjust pH to 1.0-1.5; a proper volume of fermented mash is taken, and subjects to centrifugation at 4,000 rpm for 20 min; the supernatant is filtrated through a 0.22 μm aqueous phase-filtering membrane, and the filtrate is subjected to HPLC analysis for measuring the ethanol content (v/v) (the conditions for HPLC analysis are as follows: the sample amount is 20 μL, the mobile phase is 0.005 mol/L of the HPLC-level aqueous sulfuric acid solution which is filtered through a 0.22 μm filtering membrane and degassed by ultrasonic oscillation; the flow rate is 0.6 mL/min; the column temperature is 65° C., the detector temperature is within a range of 80-85° C., the detector is a refractive index detector; the run time is 50 min).

In addition, referring to the method of the Chinese national standard GB5009.7-2016, the Fehling reagent is used for measuring the contents of residual reducing sugar in the mature fermented mash, residual total sugar in the filtrate, and the residual total sugar.

To this end, the present disclosure provides the following examples:

Calibration of the Fehling reagent: 5 mL of the Fehling reagent A and 5 mL of the Fehling reagent B are respectively taken, the Fehling reagent A and the Fehling reagent B are placed in a 250 mL triangular flask, 20 mL of water is added, 20-24 mL of 0.25% (g/g) of glucose solution is added from a burette, the mixture is uniformly mixed and then placed on an asbestos wire gauze, the mixture is heated and boiled by an electric furnace and hold for 2 min, 0.25% (g/g) of glucose standard solution is dropwise added from the burette, when the blue of the test solution disappears, 2 droplets (0.1 mL) of 1% of methylene blue indicator solution are added to reappear the blue, then the glucose solution is slowly dripped until the blue of the test solution begins to disappear and the red starts to appear, and data is recorded and the result is calculated and converted.

Measurement of the residual reducing sugar: weighing 10 g of mature fermented mash, injecting the mash into a 250 mL volumetric flask, adding water to a constant volume and subsequently mixing uniformly, filtering the aqueous solution with absorbent cotton, and taking 5 mL of filtrate to determine a content of the residual reducing sugar according to the Fehling reagent method.

Measurement of the residual total sugar in the filtrate: taking 100 mL filtrate of fermented mash for measuring the reducing sugar, adding 10 mL of 20% hydrochloric acid, converting it for 60 min in a boiling water bath, cooling and then neutralizing to be slightly acidic by using 20% sodium hydroxide solution, fixing the volume to 250 mL, filtering the solution with absorbent cotton, taking 10 mL of filtrate, and measuring the residual total reducing sugar in the filtrate according to the Fehling reagent method.

Measurement of residual total sugar: weighing 50 mL of mature fermented mash, pouring it into a 250 mL triangular flask, adding 40 mL of water and 10 mL of 20% hydrochloric acid, covering a rubber plug with a long glass tube having a length of 1.0 m at a plug opening, converting in a boiling water bath for 60 min, taking it out and cooling, neutralizing it with 20% (g/g) sodium hydroxide to be slightly acidic, transferring it into a 250 mL volumetric flask, adding water to allow the liquid surface to reach the certain scale, shaking uniformly and then filtering with absorbent cotton. Sucking 10 mL of the filtrate, adding the sucked filtrate into a triangular flask containing 5 mL of Fehling reagent A, 5 mL of Fehling reagent B and 20 mL of water, titrating with 0.25% (g/g) of glucose solution, and titrating 10 mL of the Fehling reagent with 0.25% (g/g) of glucose solution to use it as a blank.

In the present disclosure, the mature mash refers to the fermented mash obtained at the end of ethanol fermentation.

The fermentation liquor is regularly subjected to microscopic examination during the fermentation process, so as to determine the number of the yeast, the germination rate, the morphology, the condition of miscellaneous bacteria and the like.

In the present disclosure, the reference level may be derived from one or more of the starting *S. cerevisiae* or other S. cerevisiae in use. In the present disclosure, the reference level is preferably derived from the starting S. cerevisiae. The reference level may be a reference level obtained by performing a parallel assay on the starting S. cerevisiae while measuring the fermentation performance of the domesticated strain of the present disclosure. It can also be a reference level of the starting S. cerevisiae that has been determined beforehand. Moreover, it may be the reference level provided by the supplier or the prior art.

In the present disclosure, it is preferred to use a reference level obtained by performing a parallel assay on a starting S. cerevisiae while measuring the fermentation performance of the domesticated strain of the present disclosure. The measurement of fermentation performances may be performed by using the methods described above or other known methods in the art. The fermentation of the strain is likewise performed with the methods described above or known methods in the art.

The examples of fermentation methods for measuring the fermentation performance are described below:

Spreading the domesticated strain of S. cerevisiae on a plate and culturing, selecting a larger strain colony to perform cultivation in a liquid culture medium overnight; transferring the strain to a liquid culture medium (the number of yeast cells after inoculation is about $1.5 \times 10^7$-$2 \times 10^7$/mL) for overnight culture; subjecting the culture broth to a centrifugal washing, and inoculating the S. cerevisiae strain with an initial cell count of $1.5 \times 10^7$/mL into a 1 L shake flask containing 350 mL of fresh liquefied mash to carry out anaerobic fermentation for 72 hours (the stirring speed is 80 rpm, the temperature is 32° C.). In the meanwhile, carrying out anaerobic fermentation in regard to the activated starting S. cerevisiae in the same way. There are at least three parallel samples for each batch of the fermentation evaluating test.

In a preferred embodiment of the present disclosure, a strain with an increased ethanol production compared to a reference level is selected as the primary domesticated strain of S. cerevisiae. In a further embodiment of the present disclosure, a strain with an increased ethanol yield, and optionally a reduced content of residual reducing sugar, a reduced content of residual total sugar and/or an increased weight loss compared with a reference level is selected as the primary domesticated strain of S. cerevisiae.

The terms "increase", "improve" or "enhance" used herein mean an increase of at least 1% compared to a reference level (e.g., the level of the starting S. cerevisiae), such as an increase of at least about 1%, or at least about 2%, or at least about 3%, or at least about 4%, or at least about 5%, or at least about 6%, or at least about 7%, or at least about 8%, or at least about 9%, or at least about 10%, or at least about 20%, or at least about 30%, or at least about 40%, or up to and including 100%, or any amount between 1% and 100% compared to the reference level; or an increase of at least about 2-fold, or at least about 3-fold, or at least about 4-fold, or at least about 5-fold, or at least about 10-fold, or any amount between 2-fold and 10-fold, or increase at a greater amount as compared with a reference level.

The terms "decline", "decrease", or "reduce" used herein means a decrease of at least 1% as compared to a reference level (e.g., the level of the starting S. cerevisiae), such as a decrease of at least about 1%, or at least about 2%, or at least about 3%, or at least about 4%, or at least about 5%, or at least about 6%, or at least about 7%, or at least about 8%, or at least about 9%, or at least about 10%, or at least about 20%, or at least about 30%, or at least about 40%, or up to and including 100% decrease (e.g., a missing level or a non-detectable level as compared to the reference level), or an decrease of any amount between 1% and 100% as compared to the reference level.

During the primary domestication, the fermentation temperature may be 28-33° C. and the stirring rate may be 110-160 rpm, preferably 115-150 rpm, more preferably 120-130 rpm. The fermentation temperature may be 28° C., 28.5° C., 29° C., 29.5° C., 30° C., 30.5° C., 31° C., 31.5° C., 32° C., 32.5° C. or 33° C. The stirring rate may be 110-160 rpm, preferably 120-150 rpm, more preferably 130-140 rpm. The fermentation temperature is preferably the same as the initial fermentation temperature of the temperature gradient for the secondary fermentation. In the primary domestication, the stirring rate in each fermentation may be identical or different.

In a preferred embodiment, the pH of the mash may not be controlled in step 3).

In step 4), the preparation of the mature mash of seeding yeast of the primary domesticated yeast strain is described above (step 2)).

In step 5), the S. cerevisiae subjects to the secondary domestication as follows: mixing the mature mash of seeding yeast of the primary domesticated yeast strain obtained in step 4) with the liquefied mash, and fermenting the mixture until the ethanol concentration in the fermented mash reaches 12% (v/v) or more, preferably 13% (v/v) or more, replacing the fermented mash with fresh liquefied mash under a temperature gradient, and continuing fermentation, wherein the replacement proportion is 55 vol %-80 vol %, preferably 60 vol %-70 vol % of the fermented mash, the time interval of replacements is 20-30 hours, the lowest temperature of the temperature gradient is 28° C.-33° C., the highest temperature of the temperature gradient is 34° C.-38° C., the amplification of the temperature gradient is 0.5° C.-2° C. for every 18-24 times of replacement, thereby obtaining a S. cerevisiae strain which is resistant to high temperature, ethanol and fermentation substrate-inhibitors.

The mature mash of seeding yeast may be mixed with the fresh liquefied mash at a volume ratio of (20-40):(80-60) in step 4). The mixing ratio is not particularly limited in the present disclosure as long as the ethanol concentration in the fermented mash can reach 12% (v/v) or more, preferably 13% (v/v) or more. For example, in the secondary domestication, the mixing ratio of mature mash of seeding yeast of the primary domesticated yeast strain and the fresh liquefied mash may be (20-40):(80-60), preferably (25-35):(65-75), more preferably (25-30):(70-75). For example, in the secondary domestication, the mature mash of seeding yeast of the primary domesticated yeast strain may be mixed with the fresh liquefied mash in a ratio of 20:80, 23:77, 25:75, 30:70, 32:68, 35:65, 37:63, 40:60.

During the domestication process, the fermentation time for the ethanol concentration in the mash to reach 12% (v/v), preferably 13% (v/v) or more for the first time is usually 30-40 hours, such as 36 hours. In this case, the amount of the thalli can reach $1.2 \times 10^8$-$1.5 \times 10^8$/mL.

In the secondary domestication, the replacement proportion is 55 vol %-80 vol % of the fermented mash, i.e., 55 vol %-80 vol % of the fermented mash is replaced with fresh liquefied mash. In an embodiment of the present disclosure, the replacement proportion may be 55 vol %-80 vol %, preferably 60 vol %-70 vol %, e.g. 55 vol %, 56 vol %, 57 vol %, 58 vol %, 59 vol %, 60 vol %, 61 vol %, 62 vol %, 63 vol %, 64 vol %, 65 vol %, 66 vol %, 67 vol %, 68 vol %, 69 vol %, 70 vol %, 71 vol %, 72 vol %, 73 vol %, 74 vol %, 75 vol %, 77 vol %, 78 vol %, 79 vol % or 80 vol % of the fermented mash.

In the secondary domestication, the time interval of replacing liquefied mash is 20-30 hours. The time interval is primarily dependent on the time when the ethanol concentration in the fermented mash again reaches 12% (v/v) or more, preferably 13% (v/v) after replacing liquefied mash is performed, so as to place the *S. cerevisiae* in an environment of subjecting to persecution of ethanol. Typically, the ethanol concentration in the fermented mash will again reach 12% (v/v) or more, preferably 13% (v/v), within 20 hours after replacing the fermented mash in a ratio of 55 vol %-80 vol %. For example, the time interval of replacement may be 20 hours, 20.5 hours, 21 hours, 21.5 hours, 22 hours, 22.5 hours, 23 hours, 23.5 hours, 24 hours, 24.5 hours, 25 hours, 25.5 hours, 26 hours, 26.5 hours, 27 hours, 27.5 hours, 28 hours, 28.5 hours, 29 hours, 29.5 hours, or 30 hours.

The lowest temperature of the temperature gradient may be 28° C.-33° C., preferably 30° C.-32° C., the highest temperature of the temperature gradient may be 34° C.-38° C., preferably 35° C.-36° C., and the amplification of the temperature gradient may be 0.5° C.-2° C., preferably 0.5° C.-1° C., for every 18-24 times of replacements. Wherein the lowest temperature is 28° C., 28.5° C., 29° C., 29.5° C., 30° C., 30.5° C., 31° C., 31.5° C., 32° C., 32.5° C. or 33° C. The highest temperature may be 34° C., 34.5° C., 35° C., 35.5° C., 36° C., 36.5° C., 37° C., 37.5° C. or 38° C. The amplification of the temperature gradient may be 0.5° C.-2° C., preferably 0.5° C.-1° C., for every 18-24 times of replacements. For example, the temperature gradient may be amplified by 0.5° C., 1° C., 1.5° C. or 2° C. for every 18-24 times, preferably 20-22 times of replacements. The amplification of the temperature gradient may be 0.5° C., 1° C., 1.5° C. or 2° C. for every 18, 19, 20, 21 or 22 times of replacements.

In the secondary domestication, the stirring rate may be 110-130 rpm, preferably 120-130 rpm. The method of the present disclosure does not impose a particular requirement on the stirring rate as long as the fermentation material can be uniformly mixed.

In a preferred embodiment, the pH of the mash may not be controlled in step 3).

In step 5), except for the arrangement that the fermentation temperature is gradiently increased, the other fermentation conditions are preferably close to or the same as the last fermentation of the primary domestication, so as to further maintain the characteristics of high-concentration ethanol resistance and fermentation inhibitor resistance of *S. cerevisiae*, and facilitate the *S. cerevisiae* to obtain the characteristic of high-temperature resistance.

For the same reason, the selective evolution of yeast cells is a slow process, so is the adaptation of yeast to high temperature-fermentation. If the fermentation temperature of the yeast is abruptly raised, the yeast will die entirely if it is not adapted to the temperature rise. Conversely, if the domestication is continued at a certain temperature for a period of time such that the yeast adapts to the fermentation conditions at that temperature, the temperature is slowly increased, so that the yeast can adapt to the new fermentation temperature as soon as possible, thereby gradually increasing the temperature tolerance of the yeast. The slow rate of temperature rise may provide the yeast with a gradual adaptation process, if the temperature rise is too fast, the yeast is difficult to adapt to high temperature, and the death rate will be high.

Domestication is a method for directed breeding of microorganisms, wherein the microorganisms gradually adapt to a certain specific condition, and finally obtain a microorganism with higher tolerance and metabolic activity. The present disclosure preferably uses the commercially available Angel super brewing-high activity-dry yeast as an object, and develops a suitable domestication method to repeatedly obtain the *S. cerevisiae* suitable for industrial production which is resistant to fermentation substrate-inhibitor, high temperature and ethanol.

Examples

The technical solution of the present disclosure is further specified below by means of the specific examples with reference to the accompanying drawings. It shall be understood that the descriptions are only intended to further illustrate the features and advantages of the present disclosure, instead of imposing restriction on the claims of the present disclosure.

Unless otherwise specified, the raw materials and equipment used in the present disclosure are commercially available or commonly used in the art.

Each of the methods in the following examples pertains to the conventional method in the art unless otherwise specified.

Example 1

The domestication of *S. cerevisiae* is performed according to the procedure shown in FIG. 1.

The Angel super brewing-high activity-dry yeast (production batch number: cy80081) is purchased from the Angel Yeast Co., Ltd. The substrate used in the domestication process and the seeding yeast culture is liquefied mash of corn powder, and the dry solid content is 30 wt %. The domestication process is carried out in a table type-fermentation tank (Shanghai Baoxing Biological Equipment Engineering Co., Ltd, BIOTECH 2JG) with a total volume of 3 L.

The liquefied mash of corn is obtained through the following steps: mixing corn powder and water with a mass ratio of 1:2 to prepare an uniform slurry, heating up for precooking so that the starch absorbs water and swells, heating the slurry to a temperature of 85±1° C., holding for 30 min, adding amylase (Novozymes, Suhong AA Plus) to liquefy at the temperature of 85° C. for 3 hours. The liquefied mash of corn contained 125,000 U/kg (liquefied mash) saccharifying enzyme (Novozymes, Suhong GA), 3,500 U/kg (liquefied mash) acid protease (Shandong Longda Bio-products Co., Ltd., 100,000 U/mL) and 3 ppm penicillin.

(1) Weighing 10 g of Angel super brewing-high activity-dry yeast, adding it into 200 mL of sterile water, and activating for 30 min at a temperature of 30° C.

(2) Inoculating the activated *S. cerevisiae* into a yeast tank according to cell number of $1.3 \times 10^8$-$1.5 \times 10^8$ CFU/mL, and culturing under the following cultivation conditions: culturing at a temperature of 29±1° C., a pH of 4.0-5.0, a stirring rate of 200 rpm, and introducing sterile air at a rate of 480 m$^3$/h, culturing for 10 hours, thereby obtaining a mature mash of seeding yeast.

(3) 500 mL of mature mash of seeding yeast ($1.2 \times 10^8$-$1.5 \times 10^8$ CFU/mL) and 2,000 mL of liquefied mash of corn powder are added into a fermentation tank, the total volume of the fermentation reaction is 2.5 L; fermenting at a fermentation temperature of 32° C. and a stirring rate of 150 rpm in nature pH until the ethanol concentration in the mash reaches 13% (v/v) (at 36 hours of fermentation); replacing the fermented mash in the fermentation tank with fresh liquefied mash at a replacement proportion of 60 vol % and continuing the fermentation process, wherein the time interval for replacement is 24 hours, the number of replacements is 30 times, and the fermentation conditions are as follows: under the condition of nature pH, the fermentation temperature is 32° C., and the stirring rate is 120 rpm; filtering the mature mash sample with two layers of sterile gauze, sucking 1 mL of filtrate and diluting by 10 times and subjecting the diluted filtrate to a microscopic examination, when the shape of cell become plump ellipse and non-existence of miscellaneous bacteria is determined, spreading the sample on a YEPD fixed plate, selecting a plurality of larger strain colonies, performing a secondary plate culture and numbering, performing enlarge culture by using a YEPD liquid culture medium, inoculating the mash to the fresh liquefied mash of corn according to the initial cell number of $1.5 \times 10^7$/mL after the cell number reaches $2 \times 10^8$/mL, performing evaluation by anaerobic shake flask fermentation for 72 hours in a 1 L shake flask (the temperature is 32° C., the stirring rate is 80 rpm); in the meanwhile, after activating the Angel super brewing high activity dry yeast powder by water, fermenting the liquefied mash of corn of the same batch with the same inoculation amount and under the identical conditions to obtain a reference level; the primary domesticated yeast strain is screened and obtained by comparing with the reference levels.

(4) Performing primary enlarge culture for the primary domesticated yeast strain by using a YEPD liquid culture medium (the stirring rate is 80 rpm, the temperature is 32° C., and the culture time is 8 hours); subsequently inoculating the fermentation liquor after the primary enlarge culture to liquefied mash of corn powder in a volume ratio of 1:3 for performing secondary enlarge culture in a 1 L shake flask (enlarge culture condition: the stirring rate is 80 rpm, the temperature is 32° C., and the culture time is 12 hours); then obtaining mature mash of seeding yeast according to the method of step 2).

(5) Adding 500 mL of mature mash of seeding yeast ($1.2 \times 10^8$-$1.5 \times 10^8$ CFU/mL) in step 4) and 2,000 mL of liquefied mash of corn powder into a fermentation tank, wherein the total volume of the fermentation reaction is 2.5 L; fermenting at a fermentation temperature of 33° C. and a stirring rate of 120 rpm in nature pH until the ethanol concentration in mash reaches 13% (v/v); replacing the fermented mash in the fermentation tank with fresh liquefied mash at a replacement proportion of 60 vol % and continuing the fermentation process, wherein the time interval for replacement is 24 hours, the fermentation temperature starts from 33° C. and is raised by 1° C. for every 20 times of replacements until the fermentation temperature is raised to 35° C., and the fermentation conditions are as follows: under the condition of nature pH, stirring at a speed of 120 rpm to obtain a S. cerevisiae strain which is resistant to high temperature, ethanol and the fermentation substrate-inhibitors, namely the secondary domesticated yeast strain.

The evaluation for ethanol fermentation on the secondary domesticated yeast strains is performed by taking the initial yeast strain as reference yeasts according to the corresponding method in step 3).

Measurement of ethanol production: adding a suitable amount of 65% sulfuric acid to the fermented mash sample to inactivate the enzyme and adjust its pH to 1.0-1.5; taking a proper volume of fermented mash, centrifuging at 4,000 rpm for 20 min; filtering the supernatant through a 0.22 μm aqueous phase filtering membrane, subjecting the filtrate to HPLC analysis for measuring the ethanol content (v/v) (the conditions for HPLC analysis are as follows: the sample amount is 20 μL, the mobile phase is 0.005 mol/L of the HPLC-level aqueous sulfuric acid solution which is filtered through a 0.22 μm filtering membrane and degassed by ultrasonic oscillation; the flow rate is 0.6 mL/min; the column temperature is 65° C., the detector temperature is within a range of 80-85° C., the detector is a refractive index detector; the run time is 50 min.

According to the method of the Chinese national standard GB5009.7-2016, the Fehling reagent is used for measuring the contents of residual reducing sugar in the mature fermented mash, residual total sugar in the filtrate, and the residual total sugar.

The S. cerevisiae which is resistant to fermentation substrate-inhibitors, ethanol and high temperature obtained by the method of the present disclosure may be fermented at a temperature of 35° C., its fermentation results are substantially identical with those of the Angel super brewing high activity dry yeast before domestication under the condition of temperature at 32° C.; however, as compared with the fermentation result of the Angel super brewing high activity dry yeast at a temperature of 35° C., the residual reducing sugar is reduced by about 0.26, the residual total sugar in the filtration is reduced by about 0.06, the residual total sugar is reduced by 0.53, and the volume percentage (v/v) of ethanol is increased from 14.32% to about 14.68%, as shown in Table 1. Upon estimation, the fermentation results of the secondary domesticated yeast strain shown in Table 1 may generate considerable benefits when the fermentation results are amplified to a factory ethanol fermenting-production line which produces hundreds of thousands of tons of ethanol every year.

TABLE 1

| | | I | | II | |
|---|---|---|---|---|---|
| | | Yeast | | | |
| | Domestication | Primary domesticated yeast strain | Angel super brewing-high activity-dry yeast | Angel super brewing-high activity-dry yeast | Secondary domesticated yeast strain |
| Starting conditions of fermentation | Temperature (° C.) | 32 | | 35 | |
| | pH | | Nature | | |
| | Stirring speed (rpm) | | 80 | | |
| Analysis of the end of fermentation | Residual reducing sugar (g/g, %) | 0.22 | 0.28 | 0.53 | 0.27 |
| | Residual total sugar in the filtrate (g/g, %) | 0.79 | 0.96 | 1.03 | 0.97 |
| | Residual total sugar (g/g,%3 | 2.40 | 2.39 | 2.89 | 2.36 |

TABLE 1-continued

| Domestication | I | | II | |
|---|---|---|---|---|
| | Primary domesticated yeast strain | Angel super brewing-high activity-dry yeast | Angel super brewing-high activity-dry yeast | Secondary domesticated yeast strain |
| Ethanol concentration (v/v, %) | 15.13 | 14.61 | 14.32 | 14.68 |

The example mentioned above is only a preferred embodiment of the present disclosure, and does not impose limitation on the present disclosure in any form, there are other variations and modifications of the technical solution described in the claims under a premise of without exceeding the technical solution described herein.

The invention claimed is:

1. A method for domesticating *Saccharomyces cerevisiae*, comprising:
   1) activating starting *S. cerevisiae*;
   2) preparing a mature mash of seeding yeast of the starting *S. cerevisiae* using a liquefied mash;
   3) performing a primary domestication on the *S. cerevisiae*: mixing the mature mash of seeding yeast in step 2) with a liquefied mash and fermenting the obtained mixture until the ethanol concentration in the fermented mash reaches 12% (v/v) or more, replacing the fermented mash with fresh liquefied mash and continuing fermentation to obtain a primary domesticated mash, wherein the replacement is performed for at least 20 times, the replacement proportion is 55 vol %-80 vol % of the fermented mash, and the time interval of replacements is 20-30 hours; and
   separating and purifying the *S. cerevisiae* in the primary domesticated mash, and screening a *S. cerevisiae* strain with improved fermentation performance compared with a reference level as a primary domesticated yeast strain;
   4) preparing a mature mash of seeding yeast of the primary domesticated yeast strain using a liquefied mash;
   5) performing secondary domestication on the *S. cerevisiae*: mixing the mature mash of seeding yeast of the primary domesticated yeast strain obtained in step 4) with a liquefied mash, and fermenting the mixture until the ethanol concentration in the fermented mash reaches 12% (v/v) or more, replacing the fermented mash with fresh liquefied mash under a temperature gradient, and continuing fermentation, wherein the replacement proportion is 55 vol %-80 vol % of the fermented mash, the time interval of replacements is 20-30 hours, the lowest temperature of the temperature gradient is 28° C.–33° C., the highest temperature of the temperature gradient is 34° C.–38° C., the amplification of the temperature gradient is 0.5° C.–2° C. for every 18-24 times of replacement, thereby obtaining a *S. cerevisiae* strain which is resistant to high temperature, high concentration of ethanol and fermentation substrate-inhibitors,
   wherein the liquefied mash is derived from starchy biomass, and wherein the liquefied mash is added with saccharifying enzymes.

2. The method of claim 1, wherein the starting *S. cerevisiae* is Angel brewing-dry yeast.

3. The method of claim 1, wherein the starting *S. cerevisiae* is Angel super brewing-high activity-dry yeast.

4. The method of claim 1, wherein the starchy biomass is selected from the group consisting of corn, tapioca, wheat or rice.

5. The method of claim 1, wherein the starchy biomass is corn.

6. The method of claim 1, wherein in step 3), the mature mash of seeding yeast and the liquefied mash are mixed in a volume ratio of (20-40): (80-60).

7. The method of claim 1, wherein in the primary domestication, the fermenting temperature is 28-32° C., and stirring rate is 110-160 rpm.

8. The method of claim 1, wherein the number of times for replacement in step 3) is at least 30.

9. The method of claim 1, wherein in step 3), the replacement proportion is 60 vol %-70 vol % of the fermented mash.

10. The method of claim 1, wherein the improved fermentation performance compared with a reference level comprises an increase of ethanol yield and optionally a content decrease of residual total sugar and/or residual reducing sugar in the fermented mash, in comparison to the reference level.

11. The method of claim 1, wherein the concentration of saccharifying enzyme in the liquefied mash is 122,000-126,000 U/kg (liquefied mash).

12. The method of claim 1, wherein in step 5), the mature mash of seeding yeast of the primary domesticated yeast strain obtained in step 4) is mixed with the liquefied mash in a volume ratio of (20-40): (80-60).

13. The method of claim 1, wherein the stirring rate is 110-160 rpm in the secondary domestication.

14. The method of claim 1, wherein the replacement ratio in step 5) is 60 vol %-70 vol % of the fermented mash.

15. The method of claim 1, wherein the reference level is derived from one or more of:
   1) the starting *S. cerevisiae*; and
   2) other *S. cerevisiae*.

* * * * *